(12) United States Patent
Arzamastsev et al.

(10) Patent No.: US 8,440,683 B2
(45) Date of Patent: May 14, 2013

(54) PHARMACEUTICAL PREPARATION FOR TREATING DEMYELINATING DISEASES OF THE NERVOUS SYSTEM; PREPARATION PROMOTING RESTORATION OF THE MYELIN SHEATH OF NERVE FIBERS; AND A METHOD FOR TREATING DEMYELINATING DISEASES OF THE NERVOUS SYSTEM

(75) Inventors: Evgeny Venjaminovich Arzamastsev, Moscow (RU); Klavdia Ignatievna Malinovskaya, Moscow (RU); Margarita Ivanovna Mironova, Moscow (RU)

(73) Assignee: Biogen Technologies, Moscow (RU)

( * ) Notice: Subject to any disclaimer, the term of this patent is extended or adjusted under 35 U.S.C. 154(b) by 326 days.

(21) Appl. No.: 12/734,947

(22) PCT Filed: Dec. 5, 2008

(86) PCT No.: PCT/RU2008/000747
§ 371 (c)(1),
(2), (4) Date: Jun. 3, 2010

(87) PCT Pub. No.: WO2009/075607
PCT Pub. Date: Jun. 18, 2009

(65) Prior Publication Data
US 2010/0267756 A1 Oct. 21, 2010

(30) Foreign Application Priority Data
Dec. 6, 2007 (RU) .................................. 2007145037

(51) Int. Cl.
*A01N 43/42* (2006.01)
*A61K 31/44* (2006.01)

(52) U.S. Cl.
USPC ........................................................ 514/278

(58) Field of Classification Search ................... 514/278
See application file for complete search history.

(56) References Cited

U.S. PATENT DOCUMENTS
2003/0027755 A1    2/2003   Guan et al.

FOREIGN PATENT DOCUMENTS
| RU | 1713151 | 2/1995 |
|---|---|---|
| RU | 2089610 | 9/1997 |
| WO | WO 03/041655 | 5/2003 |

OTHER PUBLICATIONS

Partial Translation of RU(11)2089610.*
abstract: Bitkov V.V. Effects of berberine, glaucine, stephaglabrin, and sanquirythrine on the synaptic transmission ISSN: 0028-2561, 1991.

* cited by examiner

*Primary Examiner* — Yong Chong
(74) *Attorney, Agent, or Firm* — Knobbe Martens Olson & Bear LLP

(57) ABSTRACT

The invention relates to a pharmaceutical remedy used to treat demyelinating diseases of the nervous system. The remedy contains stephaglabrin sulfate that contributes to the restoration of the myelin sheath of nerve fibers. A method for treating demyelinating diseases of the nervous system is also disclosed.

2 Claims, No Drawings

PHARMACEUTICAL PREPARATION FOR TREATING DEMYELINATING DISEASES OF THE NERVOUS SYSTEM; PREPARATION PROMOTING RESTORATION OF THE MYELIN SHEATH OF NERVE FIBERS; AND A METHOD FOR TREATING DEMYELINATING DISEASES OF THE NERVOUS SYSTEM

CROSS-REFERENCE TO RELATED APPLICATIONS

This application is a U.S. national stage application of a PCT application PCT/RU2008/000747 filed on 5 Dec. 2008, published as WO/2009/075607, whose disclosure is incorporated herein in its entirety by reference, which PCT application claims priority of a Russian Federation application RU2007145037 filed on 6 Dec. 2007.

FIELD OF THE INVENTION

The invention relates to pharmacology, and particularly to pharmaceutical preparations used in treating neurological diseases, such as, in the first place, demyelinating diseases, for example, acute and chronic polyradiculoneuropathies, polyneuropathies with conduction blocks of dysmetabolic and toxic neuropathies, neuropathies and neuralogies of cranio-cerebral nerves, tunnel neuropathies, and so on.

BACKGROUND OF THE INVENTION

The principal functional elements of the nervous system are nerve cells or neurons that make up between 10% and 15% of the total number of cell elements in the nervous system. The remaining, greater part of the nervous system is taken up by neuroglial cells.

The function of the neurons consists in receiving signals from receptors or other nerve cells, storing and processing the information received, and sending nerve impulses to other cells—nerve, muscle, or secretory. The glial elements constituting the bulk of the nervous tissue fulfill auxiliary functions and fill up almost the entire space between the neurons. In anatomical terms, they are distinguished into neuroglial cells in the brain (oligodendrocytes and astrocytes) and Schwann cells in the peripheral nervous system. Oligodendrocytes and Schwann cells form myelin sheaths around axons (extensions of nerve cells).

Myelin is a specific kind of cell membrane surrounding the extensions of nerve cells, most of them axons, in the central and peripheral nervous systems. In chemical composition, myelin is a lipoprotein membrane consisting of a biomolecular lipid layer that lies between the monomolecular layers of protein and is spirally wrapped around the internodal segment of a nerve fiber. The principal functions of myelin include metabolic isolation and acceleration of nerve impulse conduction, along with supporting and barrier functions.

Diseases, one of the principal manifestations of which are destruction of nerve fibers and destruction of myelin, are today one of the formidable challenges facing clinical medicine, neurology above all. There has been a recognizable increase in recent years in the number of cases attended by myelin damage.

Myelin destruction may be related to biochemical defects of its structure that are, as a general rule, genetically predetermined or result from damage caused to normally synthesized myelin under the effect of various forces.

Myelin destruction is a general mechanism of the nerve tissue reacting to any damage caused to it. Nervous diseases related to myelin destruction may be divided into two main groups—myelopathies and myeloclasties. An overwhelming majority of myelopathies is related to hereditary diseases that result in genetically caused biochemical defects of myelin structure. The underlying cause of myeloclastic diseases is destruction of normally synthesized myelin under the effect of various forces, both external and internal. Division of the diseases dealt with here into these two groups is very tentative because early manifestations of myelopathies may be explained by the effect of various external factors, while myeloclasties develop, most probably, in persons who are predisposed to them.

An example of hereditary myelopathies is provided by adrenoleukodystrophies (ALD) that are related to adrenocortical insufficiency and are distinguished by active diffusive demyelination of various part of both the central and peripheral nervous systems.

The principal metabolic defect caused by this disease is the rising content of long-chain saturated fatty acids (particularly, $C-260$) that causes serious disorders in the structure and functions of myelin. Clinical manifestations include growing weakness in the legs, disorder of polyneurotic type sensitivity ("sock" and "gloves"), and coordination disorders. An efficient specific ALD treatment does not exist today, and, therefore, symptomatic therapy is used instead.

A late form of Merzbacher-Pelizaeus sudanophilic leukodystrophy, with the onset of the disease in the second decade of life, has been described. The pronounced demyelinating damage to the brain of those patients is attended by a reduced content of cholesterol esters. The patients show progressing coordination disorders, spastic pareses, and intellectual disorders.

The group of leukodystrophies is distinguished by demyelination attended by diffuse fibrous degeneration of the white matter of the brain and formation of globoid cells in the brain tissue. Among them, Alexander's disease deserves a special attention, because it is a rare disease inherited predominantly in the autosomno-recessive type. This demyelination is distinguished by that galactolipides and cerebrosides are replaced with glucolipides accumulating in myelin. Its typical manifestations are growing spastic paralyses, reduction in the acuity of vision and dementia, epileptic syndrome, and hydrocephalus.

Also listed in the group of globoid-cell leukodystrophies are Krabbe's disease and Canavan's disease. These diseases rarely develop in adulthood. In clinical terms, they are distinguished by progressing damage to myelin in different parts of the central nervous system, resulting in pareses, coordination disorders, dementia, blindness, and epileptic syndrome.

Special attention among myeloclastic diseases must be given to viral infections, with myelin destruction playing a key role in their pathogenesis. These are, in the first place, neuro-AIDS caused by the human immunodeficiency virus (HIV), and damage to the nervous system, and also tropical spinal paraparesis (TSP) caused by the HTLV-I retrovirus.

Pathogenesis of primary damage to the CNS by the above viral diseases is related to the direct neurotoxic effect of the viruses and also to the pathological effect of cytotoxic T cells, antibodies, and neurotoxic substances produced by the infected immunocytes. Direct damage to the brain in the case of HIV infection results in the development of sub-acute encephalitis with demyelinated patches.

Treatment of all viral infections is based on the use of antiviral preparations inhibiting propagation of the virus in the infected cells.

People experiencing cachexia and suffering from chronic alcoholism, severe chronic diseases of the liver and kidneys, and in cases of diabetic keto-acidosis, are likely to develop, during resuscitation, a severe demyelinating disease—acute or sub-acute central pontine and/or extra-pontine myelinolysis. In this disease, symmetric bilateral demyelination centers are formed in the subcortical nodes and stem of the brain. It is held that this process evolves from an electrolyte balance disorder, Na ions, in the first place. The risk of myelinolysis is the highest in response to fast correction of hypo-sodaemia. In clinical terms, this syndrome can take the forms of either minimal neurological symptoms or severe alternating symptoms and evolution of coma. Typically, the disease ends in death within a few weeks, but, in some cases, heavy doses of corticosteroids prevent a lethal outcome.

Chemo- and radiotherapy may be followed by an onset of toxic leuko-encephalopathy and focal demyelination, combined with multi-focal necrosis. Another possibility is development of acute, early deferred, and late demyelinating processes. These last begin within a few months or years from irradiation and are distinguished by a severe progress and polymorphous focal neurological symptomatology. A significant role is played in the pathogenesis of these diseases by autoimmune reactions to myelin antibodies, damage of oligodendrocytes, and, therefore, disturbance of remyelination processes. Toxic damage to myelin can also be observed in cases of porphyria, hypothyroidism, intoxication by mercury, lead, CO, and cyanides, in all cases of cachexia, overdoses of anticonvulsants, isoniazid, and actinomycin, and in cases of heroin and morphine drug addiction.

Special attention must be focused on a series of myelinoclastic diseases that may be regarded as specific versions of disseminated sclerosis.

Concentric sclerosis, or Ballo's disease, is a steadily advancing demyelinating disease among people in a young age. This disease causes large demyelination foci to form predominantly in the white matter of forehead lobes, sometimes involving the gray matter as well. The foci consist of alternating regions of complete and partial demyelination, with a pronounced early damage to the oligodendrocytes.

It is worthwhile to note that demyelination foci in the CNS are fairly frequently detected in patients suffering from systemic lupus erythematosus, and primary Sjögren's syndrome, attended by vasculites of different genesis and other systemic autoimmune diseases. Myelin destruction and development of autoimmune reactions to its components has been observed in many vascular and paraneoplastic processes in the CNS (E. I. Gusev and A. N. Boiko, "Demyelinating Diseases of the Central Nervous System," *Consilium-Medicum*, Volume 2, No. 2, 2000).

Treatment aimed at slowing down or stopping progressive development of diseases attended by demyelination is largely based on the perception of these diseases as autoimmune diseases. The autoimmune process is accompanied by the emergence of myelin-toxic antibodies and T lymphocyte killers destroying Schwann cells and myelin. The immune system is corrected by immunosuppressants reducing the activity of the immune system and immunomodulators altering the proportions of nervous system components. Immunosuppression and immunomodulation are intended to destroy, remove or modify the functions of lymphocytes capable of damaging myelin.

Among the methods affecting the autoimmune mechanisms of a disease, preference is given to plasmapheresis, intravenous injection of human IgG, and use of corticosteroids ("Neuropathy," edited by N. M. Zhulev, St. Petersburg, 2005).

Plasmapheresis, however, can only be performed in a hospital environment, and its application is not always justified for patients who have retained ability to move unassisted.

The use of IgG is contraindicated in cases of anaphylactic responses, and cardiac and renal insufficiency. Complications have been observed in approximately 10% of the patients treated.

Corticosteroid therapy is administered taking into consideration a patient's history of common contraindications (peptic ulcers of the stomach and duodenum, high arterial pressure, diabetes, and so on), and using preparations inhibiting development of the most frequent complications (potassium preparations, ascorbic acid, rutin, and so on).

Available literature contains references to Copaxone-Teva, a preparation of non-interferon nature (its international name is glatiramer acetate). Copaxone-Teva is an acetate of synthetic polypeptides produced by four natural amino acids— L-glumatic acid, L-alanine, L-tyrosine, and L-lysine—and have similar elements with the basic protein of myelin in chemical structure. It belongs in the class of immunomodulators and is capable of blocking myelin-specific autoimmune reactions that are basic to the destruction of the myelin sheath of nerve fibers in disseminated sclerosis. Numerous side reactions (abscesses and hematomas at injection points, elevated arterial pressure, splenomegaly, allergic reactions, apaphylaxia, arthritis, headache, depression, spasms, bronchial spasms, impotence, amenorrhea, hematuria, and so on) have been observed when the preparation is used on a clinical scale (Khokhlov, A. P., and Savchenko, Y. N., "Myelinopathies and Demyelinating Diseases," Moscow, 1991).

According to available publications, herb preparations are known to be used to prevent development of neuron demyelination, in particular, various preparations of plantain, American artichoke, chicory, dandelion, knot-grass, couch-grass, pumpkin, and immortelle, such as Polyvitachol, Polysponin, Chitochol, Chitolen. Siperpar, Tykveol, Tykveinol, and Rosoptin (Korsun, V. F., and Korsun, E. V., "Herbs to Treat Disseminated Sclerosis: A Textbook in Methodology," INFIT, Moscow, 2004).

Also known in the art is stephaglabrin sulfate (*Stephaglabrini sulfas*), a sulfate of stepharine alkaloid extracted from the tubers and roots of *Stephania glabra* (Rob) Miers, Menispermaceae family, a perennial tropical herb growing in the subtropical and tropical mountainous areas of South China, Japan, Burma, Vietnam, and India. Attempts were— undertaken in the former U.S.S.R. to introduce the plant in the subtropics of the South Caucasus, but they ended in failure. Most of the raw material is now imported from India. Known in the art is also a method for producing stephaglabrin from plant material (U.S.S.R. Inventor's Certificate No. 315,387, 1963), Known in the art is production of a *Stephania glabra* line in a suspension culture yielding a high percentage of stepharine alkaloid by synthesis. The *Stephania glabra* culture was obtained in vitro at the Medicinal Plants Institute (VILAR). A project to develop a selection system in vitro was undertaken at the Pharmaceutical Plants Institute (IFR).

The medicament based on stephaglabrin sulfate (a sulfate of stepharine alkaloid) $(C_{18}H_{19}O_3N_2)_2.H_2SO_4$, relates to proaporphine derivatives.

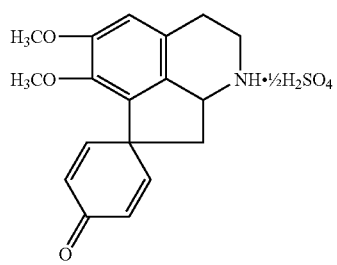

The sulfate is a white crystalline powder having a melting point of 245-246° C. (in vacuum), well soluble in water and aqueous alcohol. Stephaglabrin sulfate suppresses the activity of true and false cholinesterase, has a tonic effect on smooth muscles, and lowers arterial pressure. It has a low toxicity.

In the past, stephaglabrin sulfate was authorized for use in medical practice as an anti-cholinesterase medicament (U.S.S.R. Inventor's Certificate No. 315,388, 1963).

The inventors' continued studies showed that stephaglabrin sulfate has a specific inhibiting activity in relation to connective tissue development, preventing formation of scars as a result of damage to a nerve, and may be used as a medicament to heal traumatic and post-operation injuries to the peripheral nervous system (U.S.S.R. Patent No. 1,713, 151, 1985).

SUMMARY OF THE PRESENT INVENTION

An unexpected property of stephaglabrin sulfate discovered by the inventors and confirmed in their experiments was the ability of stephaglabrin sulfate to stimulate the growth of Schwann cells and subsequently form myelin, probably, under the effect of neuron-growth factors generated under the influence of the medicament and contributing to the restoration of the myelin sheath of a nerve fiber and, therefore, restoration of its functionality disturbed because of the damage to the nervous system (axonal degeneration, autoimmune segmentary demyelination, and primary segmentary demyelination).

Not a single of the sources known to the inventors contains references to the ability of stephaglabrin sulfate to restore the damaged myelin sheath of a nerve fiber.

DETAILED DESCRIPTION OF THE INVENTION

While the invention may be susceptible to embodiment in different forms, there are described in detail herein, specific embodiments of the present invention, with the understanding that the present disclosure is to be considered an exemplification of the principles of the invention, and is not intended to limit the invention to that as exemplified herein.

It was an object of the present invention to develop an efficient pharmaceutical remedy with minimum side effects to treat demyelinating diseases of the nervous system, find a new use for stephaglabrin sulfate, and develop a method for treating demyelinating diseases of the nervous system.

To achieve this object, the inventors have developed a pharmaceutical remedy to treat demyelinating diseases of the nervous system that contains stephaglabrin sulfate as an agent contributing to the restoration of the myelin sheath of a nerve fiber, wherein the content of stephaglabrin sulfate in the remedy varies preferably from 0.2% to 1.0%.

For further achieving this object, the inventors have proposed: a method of use of stephaglabrin sulfate, which method comprises: administration of stephaglabrin sulfate to treat demyelinating diseases of the nervous system as an agent contributing to the restoration of the myelin sheath of a nerve fiber.

Yet, for achieving this object, the inventors have also proposed: a method for treating demyelinating diseases of the nervous system, comprising: —symptomatic therapy; —electrophysiological procedures; and administering to the patient stephaglabrin sulfate as a remyelinating remedy. Stephaglabrin sulfate is administered to the patient parenterally in doses of 2 to 8 ml of 0.25% solution twice a day. The course of treatment lasts for 20 days.

The medical result of the claimed combination of objects consists in a high efficiency of the therapeutic effect of the preparation if used in small doses, reduction in the number of adverse side effects, and shorter and more efficient treatment of demyelinating diseases of the nervous system.

It has been found in experiments on rats that stephaglabrin sulfate administered within the range of preferred optimal doses of 0.1 to 1.0 mg/kg stimulates an early start of myelination of degenerating nerves, making the myelination process faster and fuller, which completes within a shorter period in comparison with animals that have not been administered the preparation.

The majority of nerve fibers in the peripheral ends of the nerves of rats receiving stephaglabrin sulfate treatment had a myelin sheath and a normal histological structure within 60 to 80 days. Subsequent electrophysiological studies showed a complete recovery of the speed of impulse passage in the nerve.

By comparison, myelination of nerve fibers proceeded slowly in control animals that were not treated with stephaglabrin sulfate and was not completed even within 100 to 120 days.

DESCRIPTION OF PREFERRED EMBODIMENTS

The following examples explain the idea of the invention without, however, restricting the scope thereof.

Example 1

Administration of stephaglabrin sulfate intramuscularly in 2.0 ml doses of a 0.25% solution twice a day for two to three weeks in treating myelopathy patients showing elements of a lateral amyotrophyic syndrome. The effects observed included disappearance of fibrillations, reduction in amyotrophy intensity and polykinetics of proprioceptive reflexes, and growth of muscle power in the arms.

The preparation was effective in patients suffering from the cerebrospinal form of disseminated sclerosis combined with tetraparesis, cerebello-ataxic syndrome, and pelvic disorders.

Example 2

The preparation was administered to 37 patients suffering from syringomyelia. A positive effect was observed in 28 patients: pain intensity diminished to the point of disappearance within 10 to 14 days of preparation administration, face sensitivity was recovering and corneal reflexes appeared, swallowing disorders were corrected, and sensitivity (to pain and temperature) was observed to be restored on the body and extremities.

The best therapeutic effect was observed in patients who were given stephaglabrin sulfate in 2 ml doses twice a day (in a course of 100 to 200 ampoules). Along with the administration of the preparation, all the patients were directed to take massage sessions, physiotherapy exercises, spine ionization by potassium iodide, and vitamins $B_1$ and $B_{12}$. It is noteworthy that the levels of sensing disorders were lowered within two to three weeks from the start of treatment. Special attention must be drawn to the fact that the malfunctions are corrected in patients showing early signs of syringobulbia. The intensity of sympathalgic pains declined (down to the point of disappearance) in some patients beginning on the 10th to 12th day of administration of the preparation.

Example 3

A positive therapeutic effect was observed following administration of stephaglabrin sulfate in 14 patients suffering from severe amyotrophic lateral sclerosis. Strength was observed to build up in the extremities in 12 patients as a result of treatment, and disorders of the bulbar functions—swallowing and breathing—were reduced.

For example, one patient suffering from amyotrophic lateral sclerosis, attended by aphonia and dysphagia, showed a significant improvement in swallowing after 10 days of injections of stephaglabrin sulfate in doses of 2 ml twice a day.

Another patient had his disordered breathing, which could not be corrected by other preparations, restored.

What is claimed is:

1. A pharmaceutical composition for restoring myelin sheath of nerve fibers in a subject, comprising 0.2 to 1.0% of stephaglabrin sulfate.

2. The pharmaceutical composition of claim 1 comprising a volume of 2 to 8 ml.

* * * * *